United States Patent
Gupta et al.

(10) Patent No.: US 10,383,623 B2
(45) Date of Patent: *Aug. 20, 2019

(54) SURGICAL FASTENER

(71) Applicant: C.R. Bard, Inc., Murray Hill, NJ (US)

(72) Inventors: Saurav V. Gupta, Medway, MA (US); Kevin J. Ranucci, Warwick, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 88 days.

This patent is subject to a terminal disclaimer.

(21) Appl. No.: 15/432,701

(22) Filed: Feb. 14, 2017

(65) Prior Publication Data

US 2017/0156724 A1    Jun. 8, 2017

Related U.S. Application Data

(63) Continuation of application No. 15/207,949, filed on Jul. 12, 2016, now Pat. No. 9,603,597, which is a continuation of application No. 14/075,325, filed on Nov. 8, 2013, now Pat. No. 9,427,232.

(51) Int. Cl.
| | |
|---|---|
| *A61B 17/064* | (2006.01) |
| *A61B 17/068* | (2006.01) |
| *A61B 17/08* | (2006.01) |
| *A61B 17/10* | (2006.01) |
| *A61B 17/00* | (2006.01) |

(52) U.S. Cl.
CPC ...... *A61B 17/064* (2013.01); *A61B 17/00234* (2013.01); *A61B 17/0682* (2013.01); *A61B 17/08* (2013.01); *A61B 17/083* (2013.01); *A61B 17/10* (2013.01)

(58) Field of Classification Search
CPC .......... A61B 2017/0647; A61B 17/064; A61B 2017/0648; A61B 17/10; A61B 2017/0649; A61B 17/068; A61B 17/08; A61B 17/07207; A61B 17/0682
USPC .......................... 606/139, 151, 115, 221, 219
See application file for complete search history.

(56) References Cited

U.S. PATENT DOCUMENTS

| | | | |
|---|---|---|---|
| 5,352,229 A | 10/1994 | Goble et al. | |
| D364,462 S | * 11/1995 | Michelson | ................... D24/145 |
| 5,720,753 A | 2/1998 | Sander et al. | |
| 5,779,707 A | 7/1998 | Bertholet et al. | |
| 6,325,805 B1 | 12/2001 | Ogilvie et al. | |
| 7,722,610 B2 | 5/2010 | Viola et al. | |
| 8,663,244 B2 | 3/2014 | Reeser | |
| 8,777,969 B2 | 7/2014 | Kayan | |
| 9,427,232 B2 | 8/2016 | Gupta et al. | |

(Continued)

FOREIGN PATENT DOCUMENTS

| | | |
|---|---|---|
| EP | 0 747 023 A1 | 12/1996 |
| WO | WO 2008/005465 A2 | 1/2008 |
| WO | WO 2010/045487 A1 | 4/2010 |

*Primary Examiner* — George J Ulsh
(74) *Attorney, Agent, or Firm* — Wolf, Greenfield & Sacks, P.C.

(57) ABSTRACT

Various embodiments of a non-deforming surgical fastener are discussed. In one embodiment, the fastener includes two legs and a backspan extending between the two legs. The fastener also includes a backspan thickness that is adapted to reduce the pressure and/or increase the holding strength applied to underlying materials. The non-deforming fastener is constructed and arranged to retain substantially the same shape before, during and after deployment into the target implantation site.

25 Claims, 6 Drawing Sheets

(56) References Cited

U.S. PATENT DOCUMENTS

| | | |
|---|---|---|
| 9,603,597 B2 | 3/2017 | Gupta et al. |
| 2004/0204723 A1 | 10/2004 | Kayan |
| 2008/0312687 A1 | 12/2008 | Blier |
| 2009/0206127 A1* | 8/2009 | Danielson ............ A61B 17/064 227/175.1 |
| 2010/0125275 A1 | 5/2010 | Kinman et al. |
| 2010/0292715 A1 | 11/2010 | Nering et al. |
| 2013/0030438 A1 | 1/2013 | Fox |
| 2013/0218177 A1 | 8/2013 | Miksza et al. |
| 2015/0133969 A1 | 5/2015 | Gupta et al. |
| 2016/0317151 A1 | 11/2016 | Gupta et al. |

\* cited by examiner

SURGICAL FASTENER

RELATED APPLICATIONS

This application is a continuation of and claims the benefit under 35 U.S.C. § 120 of U.S. application Ser. No. 15/207,949, entitled "SURGICAL FASTENER" filed on Jul. 12, 2016 which claims the benefit under 35 U.S.C. § 120 and is a continuation of U.S. application Ser. No. 14/075,325, entitled "SURGICAL FASTENER" filed on Nov. 8, 2013, each which is herein incorporated by reference in their entirety.

FIELD

Aspects relate to a surgical fastener.

BACKGROUND

Surgical fasteners are widely used in many different medical procedures. For example, staples, sutures, clips and other fasteners are commonly used in laparoscopic and open surgical procedures.

SUMMARY

According to one embodiment a surgical fastener includes a first leg, a second leg, and a backspan extending from the first leg to the second leg. The backspan includes a central pad with a thickness greater than a thickness of the backspan extending between the central pad and either the first leg or second leg. The surgical fastener is a non-deforming fastener such that the first and second legs are constructed to remain in an open position after deployment of the fastener.

According to another embodiment, a method includes: deploying a non-deforming fastener into tissue, wherein a pressure applied to the underlying tissue by the fastener is greater than or equal to 27.5 kPa and less than or equal to 275 kPa.

According to yet another embodiment, a surgical fastener includes a first leg, a second leg, and a backspan extending from the first leg to the second leg. The backspan has an area less than or equal to 10 mm$^2$ and greater than or equal to 0.25 mm$^2$. The surgical fastener is a non-deforming fastener such that the first and second legs are constructed to remain in an open position after deployment of the fastener.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
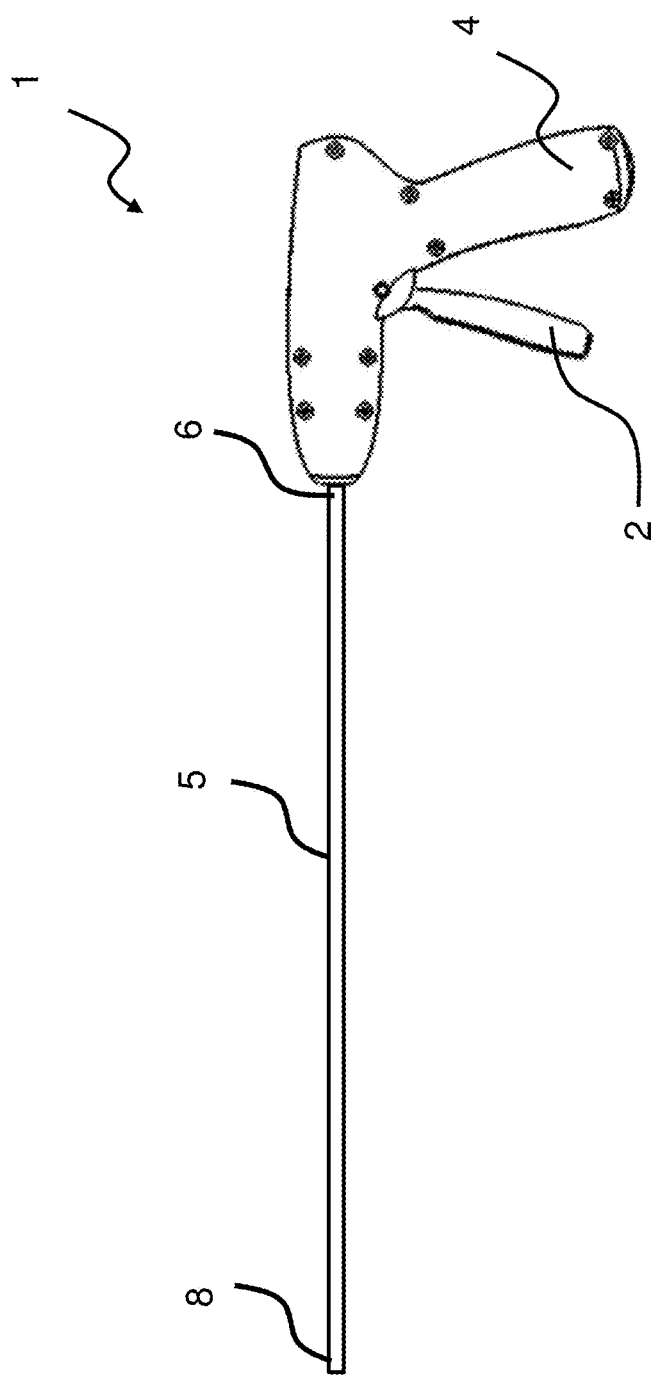
FIG. 1 depicts a surgical fastener deployment device that may be used to deploy surgical fasteners in accordance with an aspect of the invention.

The inventors have appreciated the benefits associated with a surgical fastener capable of applying reduced pressures over larger areas to an underlying prosthetic and/or tissue. For example, a surgical fastener might apply a larger total holding strength over a greater area, while subjecting an underlying prosthetic and/or tissue to a relatively low pressure during insertion. Alternatively, a surgical fastener might distribute a desired holding force across a larger area to avoid applying excessive pressure to an underlying prosthetic and/or tissue. In view of the above, the inventors have recognized that a surgical fastener including a backspan with an increased surface area may be used to provide reduced pressures and/or increased retention forces as compared to typical surgical fasteners.

Depending on the particular application, some types of surgical fasteners are designed to deform during deployment. For example, some surgical staples have legs that curl inward into a closed position as the staple is deployed into a tissue and/or prosthetic in order to secure the staple at the desired implantation site. Therefore, as used herein, a "deforming" fastener is one that is constructed and arranged to change shape as it is deployed into the target implantation site.

In contrast to the above, as used herein, a "non-deforming" fastener is one that is constructed and arranged to retain substantially the same shape before and after deployment into a target implantation site. While non-deforming fasteners may undergo some permanent deformation such as dents or shape alterations due to contact with hard materials or due to some amount of elastic deformation, the legs of such non-deforming fasteners are not designed or intended to bend or deform during normal use. Instead, the legs of the surgical fasteners are deployed in an open position and remain in the open position after deployment as well.

The surgical fasteners disclosed herein may be made from any appropriate material including various appropriate metals and polymers. Additionally, the material may be selected such that the surgical fastener is non-absorbable or bioabsorbable as the current disclosure is not so limited. For example, a non-absorbable surgical fastener may be made from: a stainless steel, such as 316L stainless steel, titanium, a nickel titanium based alloy such as nitinol, polypropylene, a high density polyurethane, ultra high molecular weight polyethylene (UHMWPE), nylon, polyester or any other appropriate material. Appropriate bioabsorbable materials include, but are not limited to magnesium, zinc, manganese and iron, or their combination alloy, polylactic acid, polyglycolic acid, copolymers thereof, and the like.

The disclosed surgical fastener may also be manufactured in any appropriate fashion. For example, the surgical fastener may be integrally formed such that the fastener comprises a single monolithic component. In other embodiments, the fastener may be assembled by forming separate portions of the fastener and attaching them together using an adhesive, a welding process, or any suitable method or substance, as this aspect is not so limited.

For the sake of clarity, the embodiments depicted in the figures are directed to a laparoscopic device. However, the current disclosure is not limited to laparoscopic devices. Instead, the currently disclosed surgical fasteners could be used in any appropriate device for the deployment of a surgical fastener into tissue. For example, the surgical fasteners could be used in an endoscopic device, a borescopic device, a catheter, a deployment device for use in "open" procedures, or any other appropriate deployment device. Additionally, a device might use any number of surgical fasteners.

For the purposes of this application, a barb associated with the surgical fastener is not considered to be part of a leg that it extends from.

Turning now to the figures, embodiments related to a non-deforming surgical fastener with a widened backspan capable of applying reduced pressures and/or increased holding strength to underlying materials is described.

FIG. 1 depicts an exemplary fastener deployment device 1 for deploying one or more surgical fasteners into a prosthetic and/or tissue. The deployment device includes a handle 4 at a proximal end of the device and an actuation button such as a trigger 2 on the handle. The deployment device also includes a shaft 5 extending in a distal direction from the handle 4. Actuating the trigger 2 moves fasteners inside shaft 5 in a direction from the proximal end 6 of the shaft to the distal end 8, and deploys a distal-most surgical fastener from the distal end 8 of the shaft 5. It should be understood that the deployed surgical fastener may be deployed into any appropriate prosthetic which may be embodied by any number of different components or materials. For example, in one embodiment, the prosthetic may be a soft tissue repair fabric, such as a surgical mesh, used for repairing a hernia.

Figure 2:
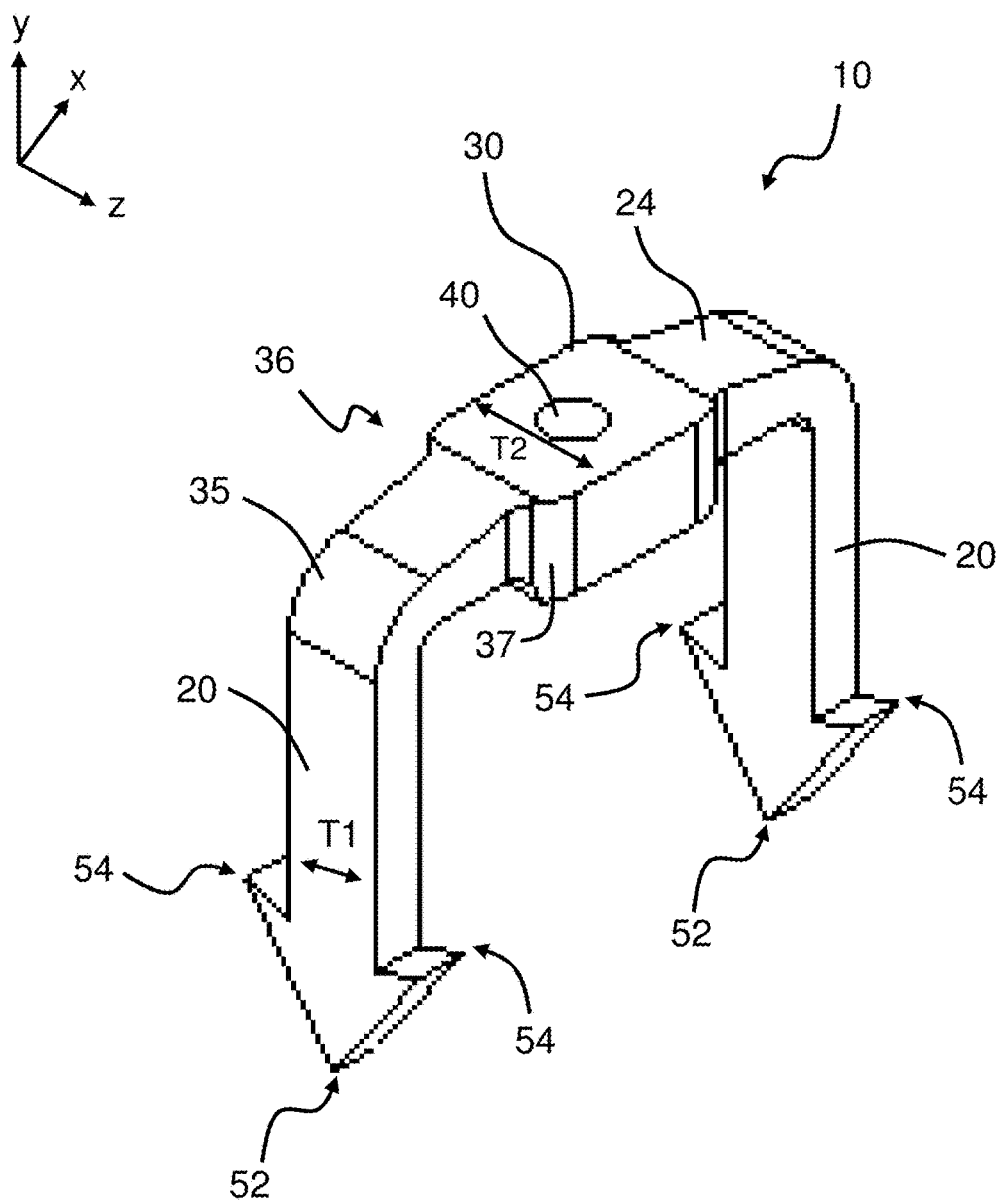
FIG. 2 depicts a perspective view of a surgical fastener in accordance with an aspect of the invention.
Figure 3:
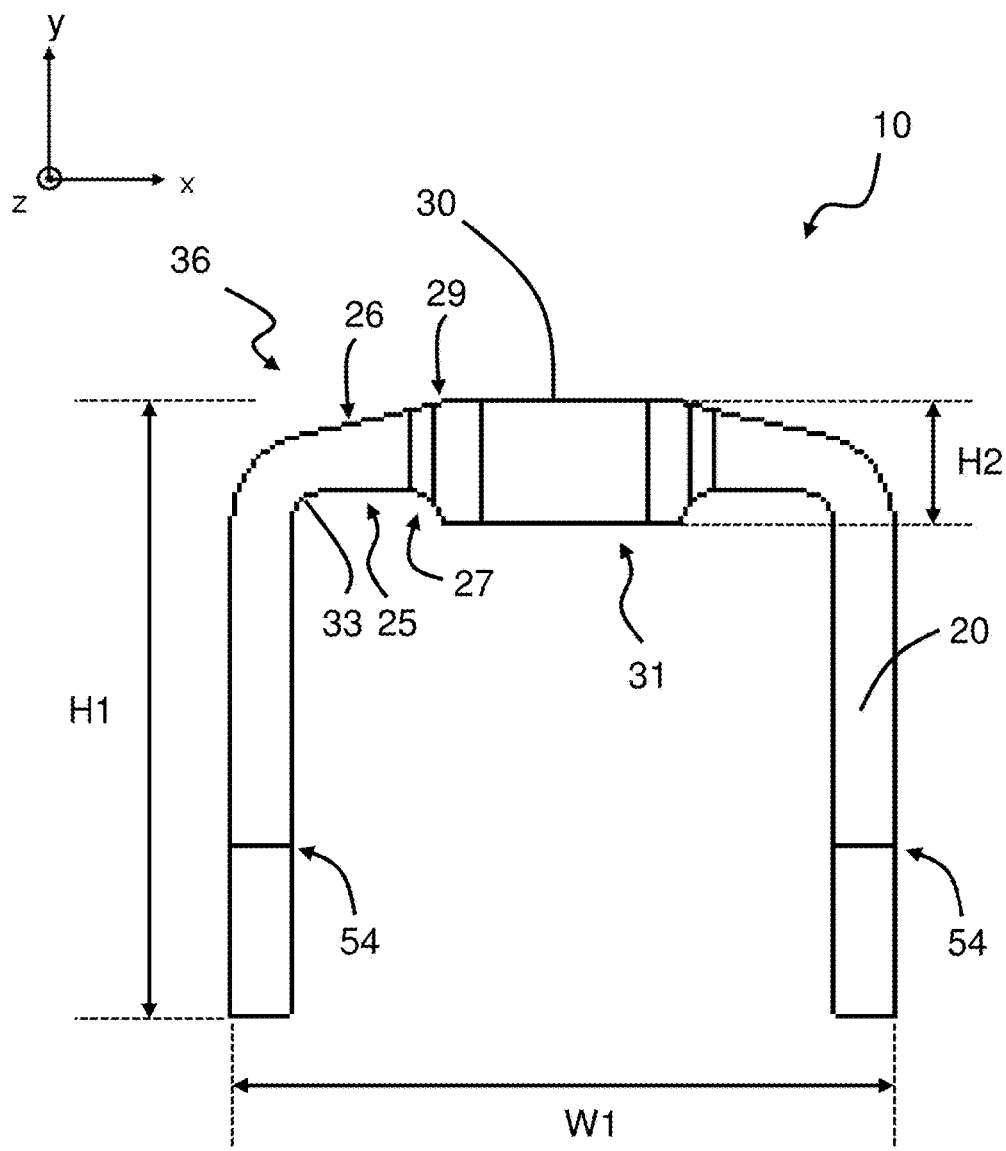
FIG. 3 depicts a front view of the surgical fastener of FIG. 2.
Figure 4:
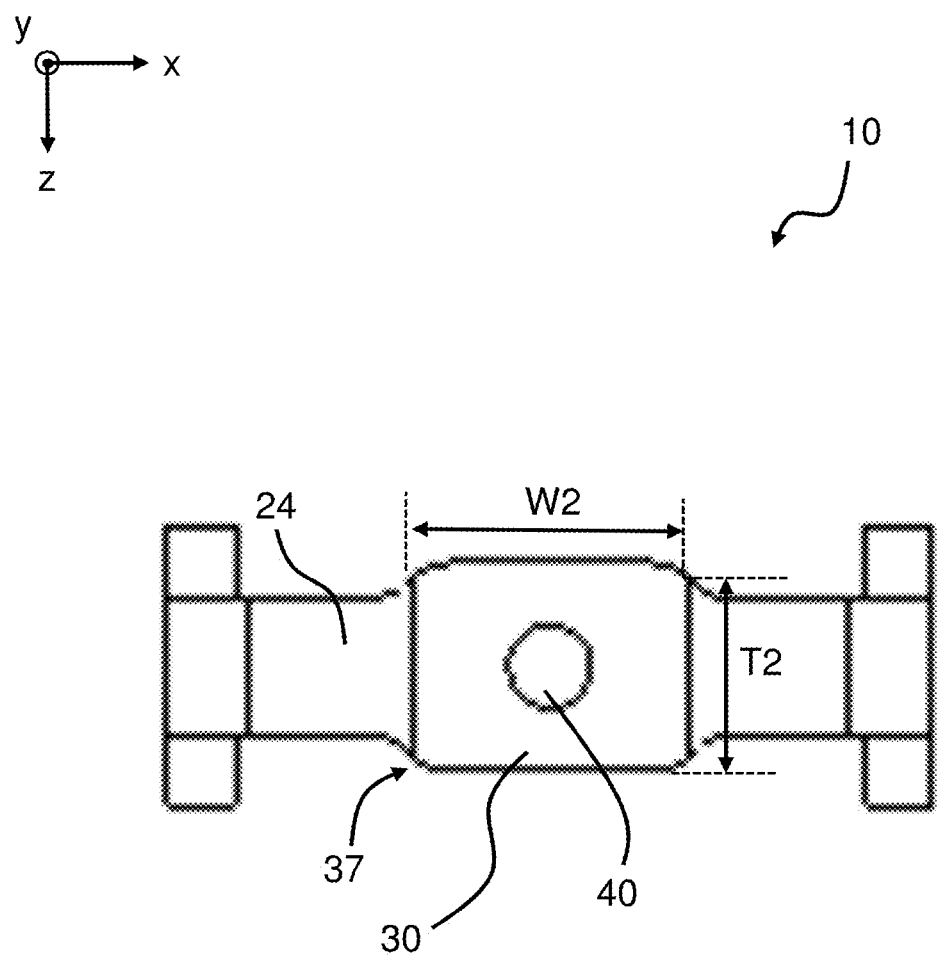
FIG. 4 depicts a top view of the surgical fastener of FIG. 2

FIGS. 2-4 depict one embodiment of a non-deforming surgical fastener 10. In the depicted embodiment, the fastener 10 has two legs 20 extending in a distal direction. While two legs are depicted, it should be understood that any number of legs might be used. Each leg 20 includes a distal tip that is adapted to be inserted into a prosthetic and/or tissue. In some embodiments, and as illustrated in the figures, the distal tips of the legs 20 include sharpened points 52 though non-sharpened points are also possible. The legs 20 are connected to opposing ends of a backspan 36 to form a surgical fastener with a somewhat U-shaped profile. Other profile shapes are also possible. For example, the surgical fastener 10 may have a C-shaped profile or any other desirable profile as the current disclosure is not limited in this fashion. As shown in FIG. 2, the legs 20 are in an open position. The legs 20 remain in the open position after deployment as well.

As seen in FIG. 2, the fastener may include outer corners 35 where the leg 20 and the backspan 36 meet. In the embodiment shown in FIG. 2, the outer corners 35 are rounded. However, in other embodiments, the outer corners 35 may be chamfered, angled or have any other suitable shape. As seen in FIG. 3, the fastener also includes inner corners 33 where the legs 20 and the backspan 36 meet. In the embodiment shown in FIG. 3, the inner corners 33 are rounded. However, similar to the above, in other embodiments, the inner corners 33 may also be chamfered, angled or have any other suitable shape.

Figure 5:
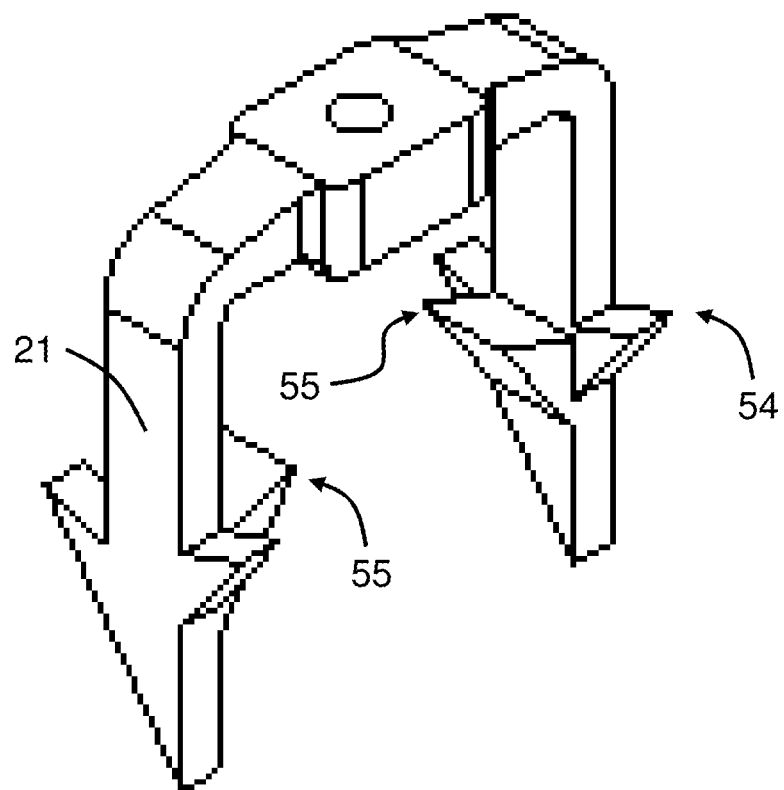
FIG. 5 depicts a perspective view of a surgical fastener with additional barbs in accordance with an aspect of the invention.

In some embodiments, the surgical fastener includes an anchoring feature such as one or more barbs to keep the fastener anchored to the underlying prosthetic and/or tissue once it has been deployed. For example, as shown in FIG. 2, barbs 54 may be located on the distal ends of legs 20 of the fastener. In the depicted embodiment, the barbs 54 point away from the distal tips 52 of the legs toward the proximal direction (away from the direction of deployment). Without wishing to be bound by theory, such barbs will increase the pull out force required to remove the fastener from the target implantation site. While the embodiment shown in FIG. 2 includes two barbs per leg, any number of barbs may be used, as this aspect is not so limited. For example, in the embodiment shown in FIG. 5, the legs have a third barb 55. In addition, barbs may be located on the legs, the backspan or on any other suitable portion of the fastener. It should also be understood that while barbs have been described above, any appropriate anchoring feature might be used including, but not limited to, surface roughness or other suitable treatment to increase the pull out force of the surgical fastener.

In some embodiments, the anchoring feature may be provided at different heights along the fastener leg. In the embodiment shown in FIG. 2, the barbs 54 are arranged at the same height along leg 20. In other embodiments, however, barbs may be arranged at different heights along the fastener legs. For example, in the embodiment shown in FIGS. 6A-6B, barbs 71 and 73 are positioned at different heights along leg 21. Without wishing to be bound by theory, barbs or other anchoring features at different heights along the fastener leg will engage with tissue and/or a prosthetic at multiple depths and may result in increased pull out resistance.

Figure 6A:
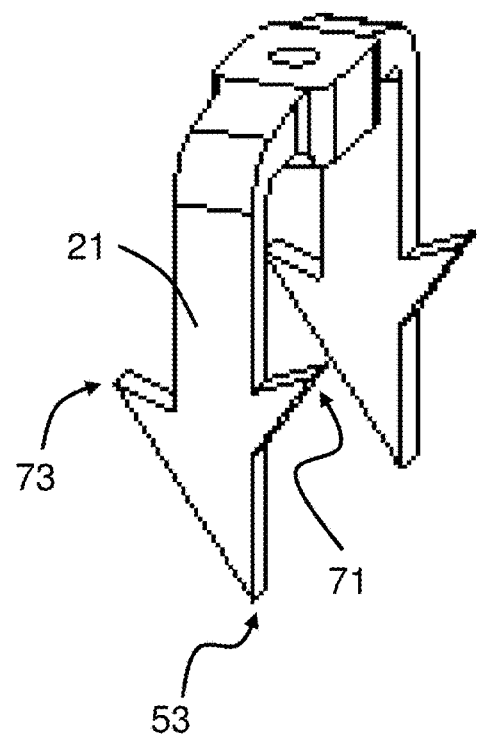
FIG. 6A depicts a perspective view of a surgical fastener with barbs arranged at different heights along the fastener leg in accordance with an aspect of the invention.
Figure 6B:
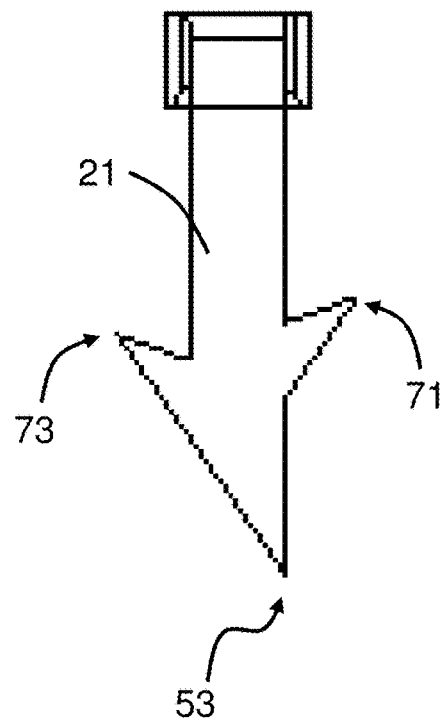
FIG. 6B depicts a side view of the surgical fastener of FIG. 6A.

It should be appreciated that the barbs shown in the figures are illustrative examples and may be varied. For example, the barbs may have longer lengths and may have any suitable angle and shape to provide pull out resistance. In addition, while FIG. 2 depicts the distal tip 52 of leg 20 as being symmetrical, the distal tip of the fastener tip may be asymmetrical. For example, as shown in FIGS. 6A-6B, the distal tip 53 of leg 21 is asymmetrical, where the left side of the tip is slanted and the right side of the tip is vertical.

The inventors have also appreciated that certain barb orientations may allow an increased width of the fastener backspan while satisfying the constraints that arise with use of the fastener within the confined space of a shaft. As shown in FIG. 3, the fastener may have a width W1 corresponding to the length between the two exterior sides of the legs 20 that is sized to be delivered through an outlet of the delivery shaft. In some cases, the barbs may be oriented to permit as wide a backspan width W1 as possible that still permits the fastener to be delivered through the outlet of the delivery shaft. As shown in FIGS. 2-3, in some embodiments, the barbs 54 may extend in a direction that is perpendicular to the width W1 (the barbs 54 extend in and out of the page in FIG. 3 along the z-axis). Having the barbs oriented in this way may permit the legs 20 to be spaced as far apart as possible within the constraints of delivery through a surgical port, thereby increasing the backspan width W1. However, other barb orientations are also possible. For example, in the embodiment shown in FIG. 5, the fastener has a third barb 55 pointed in a direction that is perpendicular to barb 54. In some embodiments, the third barb 55 points inwards towards a central axis of the fastener and thus does not increase the overall width of the fastener profile.

Depending on the embodiment, the fastener 10 may have a width W1 extending between the exterior sides of the two legs of about 4 mm to 4.9 mm, 4.1 mm to 4.8 mm, 4.2 mm to 4.7 mm, 4.3 mm to 4.6 mm, or 4.4 mm to 4.5 mm inclusive. However, it should be understood that other suitable widths are possible, as this aspect is not so limited.

As also shown in FIG. 3, the fastener may have a height H1 from a top surface of the fastener to the distal pointed tips of the legs of about 3 mm to 6.5 mm, 3.5 mm to 5 mm, or 4 mm to 4.5 mm, inclusive. However, it should be understood that other suitable heights are possible, as this aspect is not so limited.

In addition to the general structure described above, the backspan 36 can include a central pad 30. As best seen in FIG. 3, the central pad 30 may protrude downward slightly from the bottom surface 25 of the backspan. Without wishing to be bound by theory, such a protrusion 31 may help the fastener to maintain flush contact with an underlying prosthesis and/or tissue once it has been deployed. The central pad 30 may have a height H2 of about 0.25 mm to 1 mm, 0.35 mm to 0.9 mm, 0.45 mm to 0.8 mm, or 0.55 mm to 0.7 mm, inclusively. The central pad 30 may also extend between about 0 mm to 0.65 mm inclusively below the bottom surface 25 of the backspan. In other embodiments, the central pad 30 may extend inclusively between about 0.1 mm to 0.65 mm, 0.2 mm to 0.65 mm, 0.3 mm to 0.65 mm, 0.4 mm to 0.65 mm, 0.5 mm to 0.65 mm, or any other appropriate distance below the bottom surface 25. Additionally, the surgical fastener may include a transition 27 from the bottom surface 25 of the backspan to the bottom of the central pad 30 that may be curved in a concave downwards shape as depicted in the figure. However, in other embodiments, the transition 27 may be concave upwards, a flat slant, rounded, chamfered, or any other suitable shape. While the central pad 30 has been depicted as protruding below the bottom surface 25 of the backspan, it should be appreciated that in some embodiments, the bottom of the central pad may be flush with the bottom surface 25 of the backspan such that no transition between the two exists.

In some embodiments, the transition 29 from the top surface 26 of the backspan 36 to the top surface of the central pad 30 is curved. As shown in FIG. 3, in some embodiments, the transition 29 is concave downwards. In other embodiments, the transition may be concave upwards, a flat slant, rounded, chamfered, or any other suitable shape. However, it should be appreciated that in some embodiments, the top surface 26 is coplanar with the top of the central pad 30 such that no transition between the two exists.

In some embodiments, the central pad of the backspan may be thicker than each of the legs and/or a portion of the backspan attached to the central pad. For example, as shown in FIG. 2, the thickness T2 of central pad 30 may be greater than the thickness T1 of leg 20 which is also the thickness of the backspan portions attached to the central pad. In some cases, having a central pad 30 with an increased thickness T2 may increase the surface area of the fastener backspan 36, which may further reduce the pressure applied to underlying material when the fastener is deployed. In one embodiment, the legs 20 may have a thickness T1 of about 0.25 mm to 3.5 mm, 0.75 mm to 3.0 mm, 1.25 mm to 2.5 mm, or 1.75 mm to 2 mm, inclusive. The central pad 30 of the fastener may have a thickness T2 of about 0.25 mm to 3.5 mm, 0.75 mm to 3.0 mm, 1.25 mm to 2.5 mm, or 1.75 mm to 2 mm, inclusive. In some embodiments, the width W2 of the central pad is less than the width W1 of the backspan. In other embodiments, however, the width of the central pad is equal to the width of the backspan. While any appropriate width might be used, in one embodiment, the central pad may have a width W2 of about 0.25 mm to 3.5 mm, 0.75 mm to 3.0 mm, 1.25 mm to 2.5 mm, or 1.75 mm to 2 mm, inclusive.

In view of the above, the central pad may have an area between about 0.1 mm$^2$ to 10 mm$^2$, 1 mm$^2$ to 10 mm$^2$, 2 mm$^2$ to 10 mm$^2$, 5 mm$^2$ to 10 mm$^2$, or any other appropriate area. Additionally, the backspan, which includes the central pad, may have an area between about 0.25 mm$^2$ to 10 mm$^2$, 1 mm$^2$ to 10 mm$^2$, 2 mm$^2$ to 10 mm$^2$, 5 mm$^2$ to 10 mm$^2$, or any other appropriate area. Without wishing to be bound by theory, a surgical fastener including a backspan with dimensions as noted above, or other appropriate dimension, may be designed to provide a pressure that is greater than or equal to 27.5 kPa (4 psi) and less than or equal to 275 kPa (40 psi) for a particular deployment force. In other embodiments, the pressure may be between about 27.5 kPa (4 psi) to 200 kPa (29 psi), 27.5 kPa (4 psi) to 150 kPa (21.8 psi), 27.5 kPa (4 psi) to 100 kPa (14.5 psi), 27.5 kPa (4 psi) to 50 kPa (7.3 psi), or any other appropriate pressure. Typical deployment forces can be greater than or equal to about 4.4 N (1 lbf) and less than or equal to about 44 N (10 lbf). In other embodiments the deployment force may be inclusively between about 4.4 N (1 lbf) to 30 N (6.8 lbf), 4.4 N (1 lbf) to 20 N (4.5 lbf), 4.4 N (1 lbf) to 10 N (2.3 lbf), or any other appropriate deployment force.

As depicted in FIG. 4, the central pad 30 can include rounded corners 37 connecting the central pad connects to the rest of the backspan. However, the corners 37 may be any other suitable shape including chamfered, angled, or right angles as the current disclosure is not so limited.

According to one aspect, the fastener backspan width and thickness are selected to fit within a certain surgical port size while being both wide and thick enough (width being in the X-direction and thickness being in the Z direction, see FIG. 2) to reduce the pressure and/or increase the holding strength applied to underlying materials to desired thresholds. As an example, a common port size used in laparoscopic surgeries is a 5 mm port. Therefore, in some embodiments, the fastener dimensions are selected to be used with such a port.

As seen in FIGS. 2 and 4, in some embodiments, the central pad 30 of the fastener can include a through-hole 40. In such an embodiment, a mandrel or guide rod of the fastener deployment device 1 passes through the through-hole 40 of each fastener to guide and stabilize the fasteners as they are moved distally through the fastener deployment device and subsequently deployed. Alternatively or in addition to the above, the through-hole 40 may allow tissue ingrowth, which may help to stabilize the fastener at the target implantation site.

According to one aspect, the fasteners may be shaped to be stackable inside a fastener deployment device. Therefore, in some embodiments, a fastener deployment device includes a plurality of surgical fasteners that are arranged in any appropriate fashion within the shaft. When the distalmost fastener is deployed, the rest of the fasteners are sequentially advanced in a deployment direction. In some embodiments, the top surface 24 of the backspan of a fastener includes recesses (not depicted) that are shaped and arranged to receive the distal ends of the legs of a proximally located adjacent fastener (not depicted). Receiving and retaining the legs of one fastener within the recesses of an adjacent fastener may help to decease lateral slippage between adjacent fasteners as they are advanced distally through the fastener deployment device. As a result, such a stacking feature may help fasteners to remain aligned within a fastener deployment device as the fasteners are advanced. While a particular arrangement is described above, any suitable stacking feature may be used, as this aspect is not so limited.

It should be appreciated that the fasteners shown in FIGS. 2-4 are illustrative embodiments, and that other arrangements are possible. Specifically, the fastener may have more than two legs. In such an embodiment, the fastener may have three or more legs, or any other number of legs, that are evenly spaced from one another. For instance, if the fastener has three legs, the legs could be spaced 120° apart from one another. Similarly, if the fastener has four legs, the legs could be spaced 90° apart from one another. Alternatively, the legs might be spaced at regular intervals according to length. However, in other embodiments, the legs may be spaced at irregular intervals.

The above aspects and embodiments may be employed in any suitable combination, as the present invention is not limited in this respect.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising:
   deploying a non-deforming fastener into a tissue out of an elongated shaft of a fastener deployment device, the non-deforming fastener having a first leg, a second leg, and a backspan extending from the first leg to the second leg, the first and second legs extending transverse to the backspan, the backspan including a central pad with a thickness greater than a thickness of the backspan extending between the central pad and at least one of the first leg and the second leg, wherein the central pad has a width extending in a direction between the first and second legs, and the thickness of the central pad is measured in a direction transverse to the width of the central pad and to a direction in which the first and second legs extend; and
   maintaining the first and second legs in a straight configuration transverse to the backspan while deploying the non-deforming fastener into the tissue from the elongated shaft.

2. The method of claim 1, wherein deploying the non-deforming fastener includes deploying the non-deforming fastener having an area of the central pad less than or equal to 10 mm$^2$ and greater than or equal to 0.1 mm$^2$.

3. The method of claim 1, further comprising anchoring the non-deforming fastener into the tissue via at least one anchoring feature of the non-deforming fastener.

4. The method of claim 3, wherein the at least one anchoring feature comprises a first barb that points in a first direction that is perpendicular to the direction of a longest dimension of the backspan.

5. The method of claim 4, wherein the at least one anchoring feature comprises a second barb that points in a second direction that is perpendicular to the direction of a longest dimension of the backspan and opposite the direction of the first barb.

6. The method of claim 1, wherein the non-deforming fastener has at least one through-hole in the central pad of the backspan.

7. The method of claim 6, further comprising guiding and stabilizing the non-deforming fastener with a rod that passes through the through-hole of the non-deforming fastener as the non-deforming fastener is moved distally.

8. The method of claim 1, further comprising positioning at least a portion of a leg of a second fastener in a recess in a top surface of the backspan.

9. The method of claim 1, wherein a width of the backspan is between or equal to 4 mm and 4.9 mm.

10. The method of claim 1, further comprising applying a pressure to underlying tissue during deployment via an area of the backspan and central pad when a deployment force is applied to the fastener, wherein the pressure is greater than or equal to 27.5 kPa and less than or equal to 275 kPa.

11. The method of claim 1, further comprising applying a deployment force to the non-deforming fastener to deploy the non-deforming fastener.

12. The method of claim 11, wherein the backspan has an area less than or equal to 10 mm$^2$ and greater than or equal to 0.25 mm$^2$.

13. The method of claim 12, wherein the deployment force is greater than or equal to 4.4N and less than or equal to 44N.

14. The method of claim 1, wherein the backspan and central pad are monolithically formed.

15. The method of claim 1, and wherein the central pad protrudes downward past a bottom surface of the backspan.

16. The method of claim 1, wherein the non-deforming fastener includes first and second outer corners arranged so that the first leg meets the backspan at the first outer corner and the second leg meets the backspan at the second outer corner.

17. The method of claim 1, wherein the thickness of the backspan at a location where the backspan extends out from the central pad towards the first leg and/or the second leg is less than the thickness of the central pad.

18. The method of claim 1, further comprising guiding and stabilizing the non-deforming fastener with a rod that passes through a through hole formed in the central pad as the non-deforming fastener is deployed into the tissue from the elongated shaft.

19. A method comprising:
    deploying a non-deforming fastener into a tissue out of an elongated shaft of a fastener deployment device, the non-deforming fastener having a first leg, a second leg, and a backspan extending from the first leg to the second leg, the first and second legs extending transverse to the backspan, the backspan including a central pad protruding downward past a bottom surface of the backspan; and
    maintaining the first and second legs in a straight configuration transverse to the backspan while deploying the non-deforming fastener into the tissue from the elongated shaft.

20. The method of claim 19, wherein the central pad has a thickness greater than a thickness of the backspan extending between the central pad and at least one of the first leg and the second leg, and wherein the central pad has a width extending in a direction between the first and second legs, and the thickness of the central pad is measured in a direction transverse to the width of the central pad and to a direction in which the first and second legs extend.

21. The method of claim 20, wherein the thickness of the backspan at a location where the backspan extends out from the central pad towards the first leg and/or the second leg is less than the thickness of the central pad.

22. The method of claim 19, further comprising guiding and stabilizing the non-deforming fastener with a rod that passes through a through hole formed in the central pad as the non-deforming fastener is deployed into the tissue from the elongated shaft.

23. A method comprising:
   deploying a non-deforming fastener into a tissue out of an elongated shaft of a fastener deployment device, the non-deforming fastener having a first leg, a second leg, and a backspan extending from the first leg to the second leg, the first and second legs extending transverse to the backspan, the backspan including a central pad disposed between the first and second legs such that a first portion of the backspan extends between the central pad and the first leg and a second portion of the backspan extends between the central pad and the second leg;
   guiding and stabilizing the non-deforming fastener with a rod that passes through a through hole formed in the central pad as the non-deforming fastener is deployed into the tissue from the elongated shaft; and
   maintaining the first and second legs in a straight configuration transverse to the backspan while deploying the non-deforming fastener into the tissue from the elongated shaft.

24. The method of claim 23, wherein the central pad has a thickness greater than a thickness of the backspan extending between the central pad and at least one of the first leg and the second leg, and wherein the central pad has a width extending in a direction between the first and second legs, and the thickness of the central pad is measured in a direction transverse to the width of the central pad and to a direction in which the first and second legs extend.

25. The method of claim 24, wherein the thickness of the backspan at a location where the backspan extends out from the central pad towards the first leg and/or the second leg is less than the thickness of the central pad.

* * * * *